United States Patent [19]  [11] 4,052,285
Dobson  [45] Oct. 4, 1977

[54] ION SELECTIVE ELECTRODES

[75] Inventor: John Vincent Dobson, Hartlepool, England

[73] Assignee: National Research Development Corporation, London, England

[21] Appl. No.: 560,238

[22] Filed: Mar. 20, 1975

[51] Int. Cl.² ...................... G01N 27/46; G01N 27/36
[52] U.S. Cl. ............................... 204/195 G; 204/1 T; 204/195 M
[58] Field of Search .............. 204/195 G, 195 M, 1 T, 204/1 H, 1 A

[56] References Cited

U.S. PATENT DOCUMENTS

| 3,562,130 | 2/1971 | Hoole et al. | 204/195 M |
| 3,590,810 | 7/1971 | Kopecky | 204/195 M |
| 3,709,811 | 1/1973 | Saunders | 204/195 M |
| 3,717,565 | 2/1973 | Doyle | 204/195 G |
| 3,755,124 | 8/1973 | Frant et al. | 204/195 M |
| 3,806,438 | 4/1974 | Higashiyama et al. | 204/195 M |
| 3,856,649 | 12/1974 | Genshaw et al. | 204/195 M |
| 3,879,279 | 4/1975 | Baucke | 204/195 M |
| 3,909,384 | 9/1975 | Jasinski et al. | 204/195 M |
| Re. 24,222 | 9/1956 | Patnode et al. | 204/195 M |

FOREIGN PATENT DOCUMENTS 492,936   9/1938   United Kingdom ............ 204/195 G Primary Examiner—T. Tung
Attorney, Agent, or Firm—Cushman, Darby & Cushman

[57] ABSTRACT

Ion sensitive electrodes particularly for use at high temperatures and pressures are described. The electrodes can either include finely divided ion sensitive material in a matrix of low conductivity material, or a thin sheet of a naturally occurring ion sensitive material such as a mica or a silicate. The finely divided ion sensitive material may be an ion sensitive glass. Various forms of electrodes some including reference electrodes are described.

32 Claims, 21 Drawing Figures

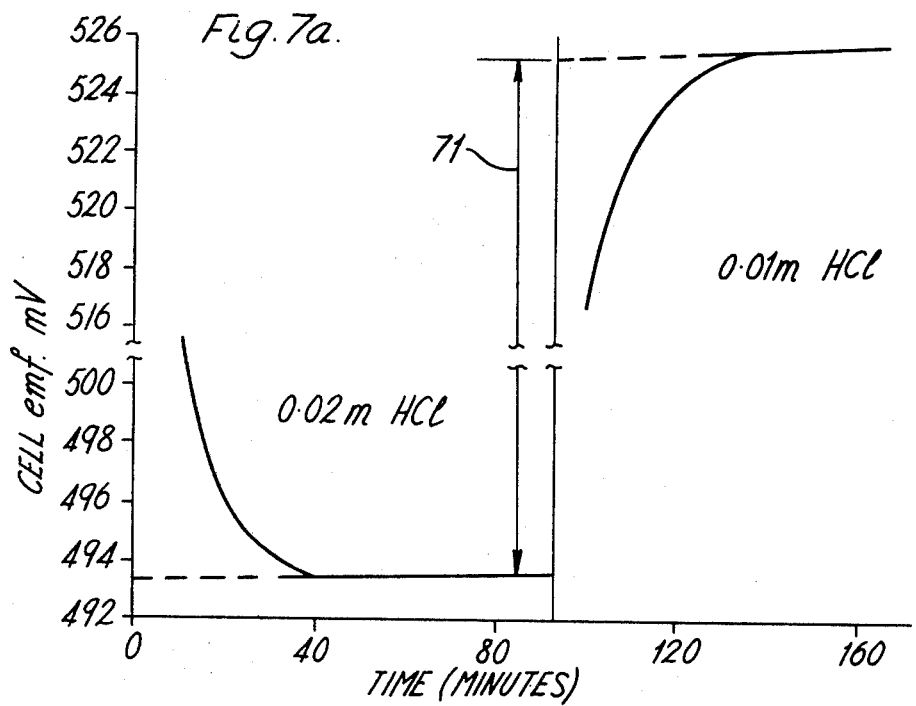
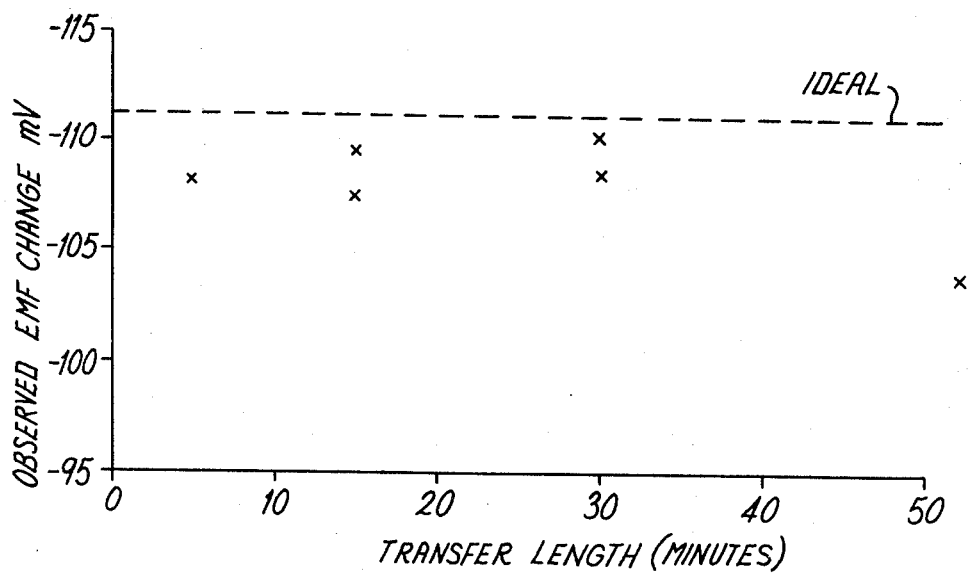

ION SELECTIVE ELECTRODES

This invention relates to ion selective electrodes and particularly, but not exclusively, to electrodes which are sensitive to the $H^+$ and $Na^+$ ions.

The ability of certain glasses, when blown into thin walled bulbs, filled with an aqueous electrolyte and also containing a reference electrode, to be sensitive to pH change is well known.

It is also well known that all available commercial glass electrodes very quickly suffer mechanical failure if the electrolyte media is aggressive, e.g. concentrated acid or alkali, especially at temperature in excess of 150° C. This catastrophic failure is due to attack on the thin walled glass bulbs by the media.

Although pH glasses that can withstand aggressive conditions are known, they are unfortunately prone to devitrification and hence present difficulties when being blown into glass bulbs. A problem in making conventional shaped and filled glass electrodes suitable for high temperature use is the inability to make them strong enough to withstand the external or internal pressures. Any attempt at thickening of the walls of the bulbs would increase the electrical resistance from about $10^6$ to $10^8$ ohms to too great a value, say greater than $10^{10}$ to $10^{12}$ ohms, for simple use.

The conventional glass electrode owes its pH response to the ability of the glass used for the bulb to readily form hydrated silicates, giving the so-called gel layer on the surface. See G. Eisenman, G. Mattock, R.G. Bates and S.M. Friedman, "The Glass Electrode", Interscience, New York (1965), also "Glass Electrodes for Hydrogen and other Cations", G. Eisenman (Ed.) Dekker, New York (1967). These hydrated silicates on the surface act as weak acids and ionize furnishing $H^+$ ion. A pH-relationship between the $H^+$ ion in solution and the $H^+$ ion in reactions at the surface of the electrode may then be formed and confer a pH sensitivity to the electrode as a whole. Conduction of charge to the reference electrode contained in the inner filling electrolytic is thought to proceed by various electrolytic mechanisms. By variation of the composition of the bulb glass a glass electrode may be made which is predominantly sensitive for example to $Na^+$ and not $H^+$. Similar weak acid associations as well as ion exchange mechanisms may be invoked in the explanations of the $Na^+$ sensitivity.

According to a first aspect of the present invention there is provided an ion sensitive electrode, including a matrix of low electrical conductivity material containing particles of an ion sensitive material, and contact means for allowing electrical coupling with the interface formed when the matrix is in contact with a liquid.

The ion sensitive material may be finely divided ion sensitive glass, such as one of the following depending on the ion to be detected: soda glass, borosilicate glass, a mixed alkali lead glass, a ternary glass, lithia glass, alkali-silicate glass, and an alkali-alkaline earth glass.

The ion sensitive material may be sensitive to the $H^+$ ion, for example the following glasses may be used in finely divided form: Corning triple purpose glass (27 to 29 mole % $Li_2O$, 2 to 4 mole % $Cs_2O$ and/or $Rb_2O$, 4 to 7 mole % $La_2O_3$, 1 mole % $UO_2$ and balance $SiO_2$). Corning 015 glass (22 mole % $Na_2O$, 6 mole % $CaO$ and 72 mole % $SiO_2$) and Perley glass (65% $SiO_2$, 28% $Li_2O$, 4% $La_2O_3$ and 3% $Cs_2O_3$ by weight). However where the ion sensitive electrode is to be used at high temperatures, a high temperature (HTD) glass having for example the composition 55% $SiO_2$, 27% $CaO$, and 18% $Li_2O$, by weight, is preferable. Each of the percentages for the composition of HTD glass may be varied by up to ± 5%. Other suitable materials for such conditions include finely divided naturally occurring micas such as ruby mica, and silicates.

In another form the ion sensitive electrode may be sensitive to $Na^+$ ions and in this case the ion sensitive material may be a finely/ divided soda glass (mentioned above), for example a glass which is similar to Corning 015 glass, having the following composition: 21.4% $Na_2O$, 6.4% $CaO$, and 72.2% $SiO_2$ (usually Indian quartz), by weight.

Finely divided ternary glasses may be used for detecting different ions provided the conditions mentioned below are met. Such glasses may contain $SiO_2$ and $Na_2O$ or $Li_2O$ together with one of the following compounds: $K_2O$, $SnO_2$, $B_2O_3$, $ZnO_2$, $Al_2O_3$ and $Ga_2O_3$. Alternatively suitable ternary glasses include three compounds each chosen from a different one of the following four groups (a) to (d): Group (a) $Sb_2O_3$, $TiO_2$, $ZrO_2$, $GeO_2$, $SnO_2$ and $PtO_3$; Group (b) $CaO$, $MgO$ and $BeO$; Group (c) $La_2O_3$, $Nb_2O_3$ and $Y_2O_3$; and Group (d) $Al_2O_3$, $B_2O_3$, $Ga_2O_3$ and $Fe_2O_3$.

Each glass used in an ion sensitive electrode must have an electrical specific resistivity of less than $10^{12}$ Ohm centimeters, the glass must not dissolve readily in the electrolyte in which it is to be used, and the glass must not devitrify easily.

Finely divided forms of ternary glasses containing oxides of elements of the fourth and fifth groups of the periodic table, such as $SnO_2$, $ZrO_2$, $TiO_2$ may be used to form electrodes sensitive to the $K^+$ and $Na^+$ ions. Similarly finely divided ternary glasses containing oxides of trivalent elements such as $La_2O_3$, $Nd_2O_3$ and $Y_2O_3$ may be used in making $Li^+$ sensitive electrodes according to the first aspect of the invention. Other glasses suitable for use in making such electrodes sensitive to the ions mentioned above and other ions will be found in the book "Glass Electrodes for Hydrogen and other Cations", Edited by George Eisenman 1967, published Edward Arnold.

One of the main advantages of electrodes according to the present invention is that such electrodes can be used at higher temperatures and pressures then the conventional glass electrodes, since the strength of the electrode at high temperature does not depend on that of the ion sensitive material and being solid instead of hollow the pressure problem becomes unimportant. This is particularly true where the ion selective material is HTD glass or mica, since these materials themselves withstand adverse conditions without substantial change.

Another advantage of glasses according to the invention is that they may be used in agressive media for comparatively long periods before deterioration is catastrophic.

Electrodes according to the invention may have emfs which are close to the ideal for a hydrogen electrode that is emf (E) response (i.e. change in emf with change in pH) $E/\Delta pH \approx 59.1$ mV/pH at 25° C, or $E/\Delta pa_{H^+} \approx 55$ mV/$pa_{H^+}$ at 25° C., but this depends on the percentage by weight of ion sensitive material in the matrix and on the type of ion sensitive material used. For example, a glass, such as Corning triple purpose glass, which has ideal response when used in a conventional electrode can also be used to make a nearly ideal response electrode according to the present inventions, provided the matrix contains at least 50% by weight of the glass.

However electrodes with potentials which are diminished from the ideal are also useful, since although their response is diminished it is still dependent on ion concentration. The application of simple types of solid state operational amplifiers, as used with some commercial (ORION) low-response types of electrodes, to bring the response up to ideal is easily possible. An example of use could be in temperature compensations for conventional glass electrodes as an inner reference. In addition, because of the very low pH response it could be neglected or compensated electrically for use in solutions of varying pH and therefore considered as a reference source of potential in a combination of other types of electrodes.

Although conventional glass electrodes have a high resistance, the same order of resistance can be achieved with electrodes according to the present invention, provided the concentration of ion sensitive material is reasonably high, say at least 40% to 50% by weight.

Preferably the low conductivity material has a specific resistance in the range $10^9$ to $10^{12}$ Ohm cms.

A number of resins are satisfactory as the low conductivity material for low temperature work, for example an epoxy resin such as AY 103 with hardener HY 951, but for electrodes used in excess of 100° C. a high temperature epoxy resin may be used, the preferred one being Araldite AY 103 with hardener HT 972. Another suitable matrix material for high temperatures is silicone rubber SR 300. Other resins which may be used include the following Araldites: AT1 or AU1, AZ15 and HZ15, or AY105 and HT972; or Epoxy Resin (Dielectric Limited 3M) No. 232 Brown or No. 252 Brown; or Polyurethane 221. Clearly any resin used must not be attacked by the electrolyte in which the ion sensitive electrode is used.

The contact means may be conductive planar member in contact with the matrix on at least one side and having an electrical connection thereto. The conductive material is preferably platinum or copper. The matrix and the planar member may be positioned in an aperture in a resin sheet, which may for example be an annular disc. In another form two such sheets or discs may be used with the planar member extending into a silicone rubber filled space between the sheets or discs, one aperture being filled with the matrix material, and the electrical connection passing through the other aperture which is filled with silicone rubber.

Instead the contact means may include a chamber for an electrolyte containing an electrode, at least part of the interior chamber wall being formed by the matrix of low conductivity material.

The ion sensitive electrode may be in other forms, for example it may comprise a wire coated with the matrix containing ion sensitive material; or the matrix may be painted on to the metallised surface of a ceramic. If the ceramic is cast with the same radius as the interior of a pipe, it is suitable, when fixed inside the pipe, for monitoring a selected ion concentration in liquid flowing along the pipe.

Where a probe including an ion sensitive electrode and a reference electrode is required, the ion sensitive material may be coated on the outside of a container with an electrical connection passing through the interior of the container. The reference electrode may then be located in one exterior wall of the container. For example if the container is a cylinder the reference electrode may form one end wall and the connection thereto may also pass through the interior of the cylinder. Instead the reference electrode may be within the container inside a further container, coupled, for example, through a porous connection to the exterior of the cylinder. In operation the further container is filled with a suitable electrolyte for the reference electrode.

According to a second aspect of the present invention there is provided an ion sensitive electrode, including a thin sheet of a naturally occurring material chosen from: ruby mica, a mica other than ruby mica, a silicate, and silicon dioxide, and contact means for allowing electrical coupling with the interface formed when one side of the mica sheet is in contact with a liquid.

The means for allowing coupling with the interface may include an electrical conductor fixed, for example, by fusing to the mica sheet. Instead the contact means may include a chamber for an electrolyte containing an electrode, at least part of the chamber wall being formed by the mica sheet.

The mica sheet may be in the form of a disc held in a gasket between two members of a holder, the gasket and the holder being of inert material and the two members of the holder being pressed together when held in a specially constructed cell. Instead a disc shaped sheet of mica may be fixed to an annular silica disc using a resin, or the mica may be held between two annular silica discs again by means of resin. Any part of the silica disc or discs which are likely to be in contact with an electrolyte are coated with an inert material.

Electrodes according to either aspect of the invention may, of course, be used in ion concentration measuring cells but the electrodes, particularly the disc electrodes, may be used as part of the cell walls. For example a cylindrical container which includes a reference electrode may have an end wall which is formed by a disc electrode held in place by a pressure fitting. Where, with electrodes according to the second aspect of the invention, the contact means is an electrolyte containing cell, the mica sheet may divide two similar such cells, one of which in operation contains the electrolyte whose ion concentration is to be measured. Such arrangements where the electrode is part of the cell walls are well suited for industrial or analytical flowing electrolyte conditions. A constant solution in one compartment would be employed in the case of the two compartment cell.

Certain embodiments of the invention will now be described by way of example, with reference to the accompanying drawings, in which:

FIGS. 1(a) and 1(b) show disc electrodes according to the first aspect of the invention.

Figure 6A:
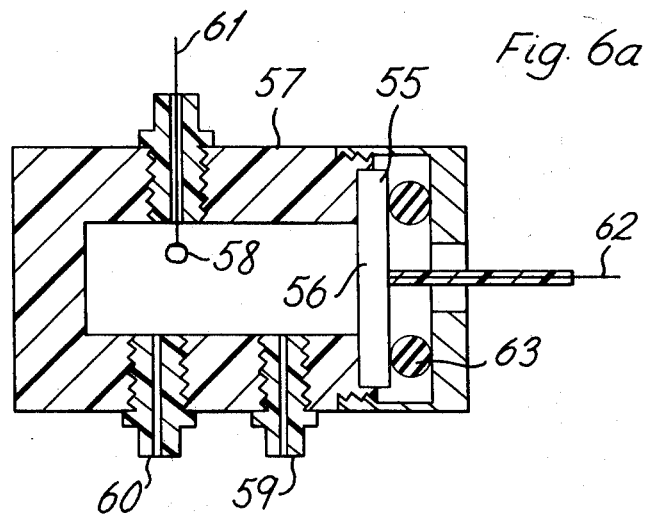
Figure 6B:
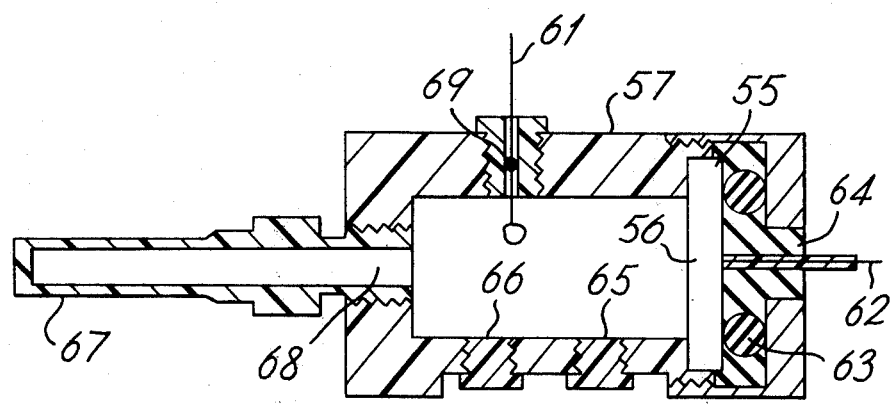
Figure 8:
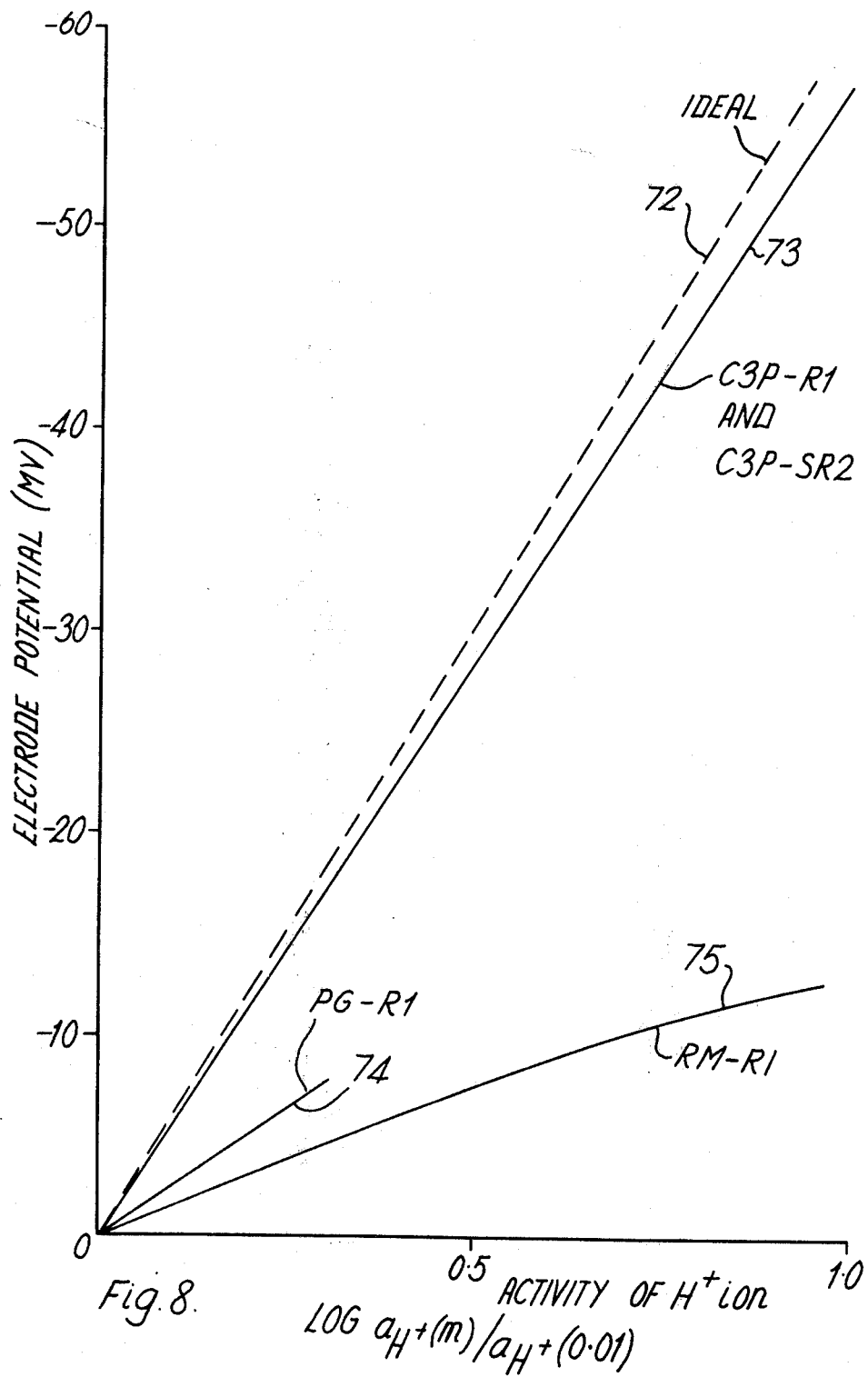
Figure 9:
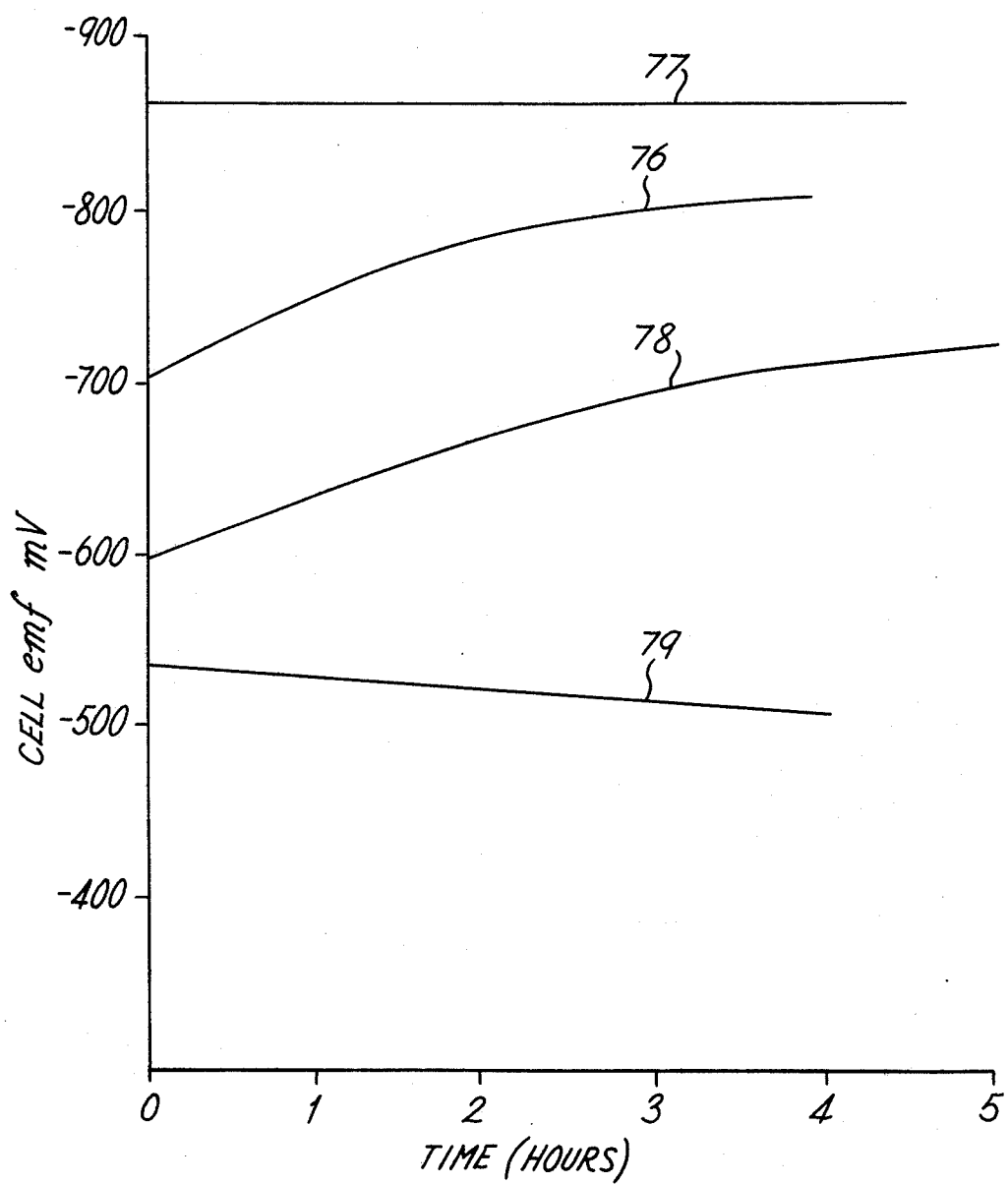
Figure 10A:
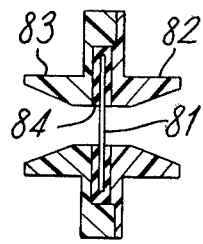
Figure 10B:
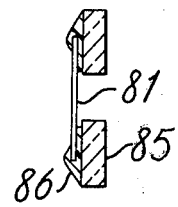
Figure 10C:
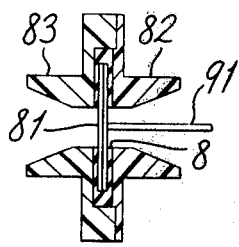
Figure 10D:
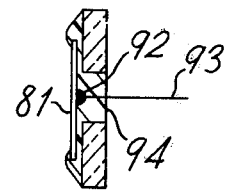
Figure 10E:
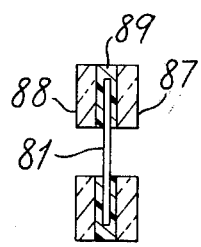
Figure 10F:
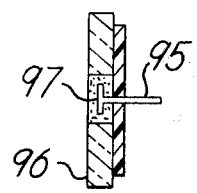
Figure 11A:
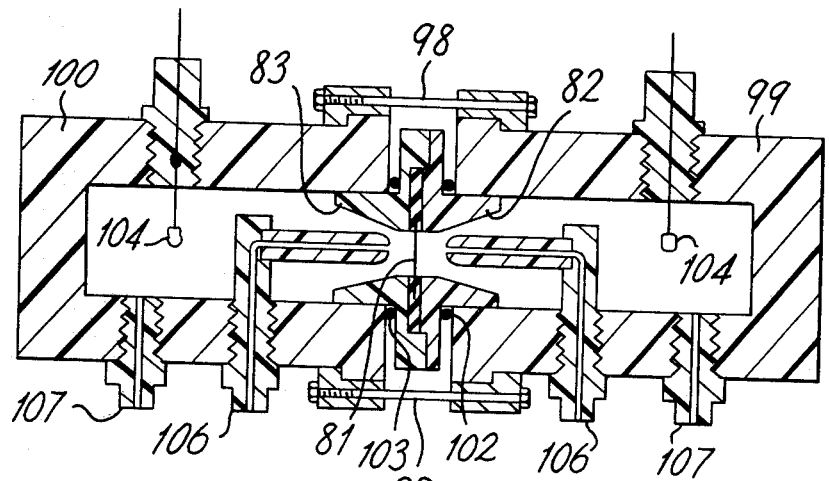
Figure 11B:
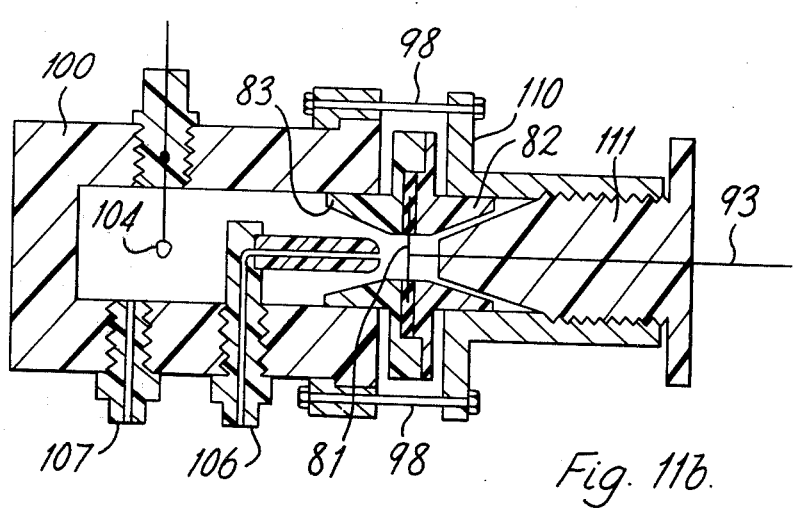

FIGS. 6(a) and 6(b) show ion concentration measuring cells with electrodes according to the first aspect of the invention, FIG. 7(a) is a graph giving the response of the cell of FIG. 6(a) to various changes in H+ ion concentration, FIG. 7(b) is a graph showing the relationship between EMF change and transfer time for a certain transfer cell, FIG. 8 is a graph giving the electrode potentials of various electrodes according to both aspects of the present invention, FIG. 9 is a graph showing the stability of cells containing electrodes according to the first aspect of the present invention, FIGS. 10(a) to 10(f) show disc electrodes with diminished response according to the first and second aspects of the present invention, and FIGS. 11(a) and 11(b) show measuring cells primarily for use with the electrodes of FIGS. 10(a) to 10(f).

The preparation of some types of ion sensitive material will first be described and then types of matrix material discussed.

As has been mentioned, the ion sensitive material may be a naturally occurring mica or silicate in finely divided form, or HTD glass, Perley glass, Corning triple purpose glass, or a soda glass equivalent to Corning 015 glass. The composition of the HTD was chosen after reference to the composition region for useful pH electrode glasses in the $Li_2O$ — $CaO$ — $SiO_2$ system mentioned in U.S. Patent Specification 2,462,843. A composition diagram showing a useful region of electrode glasses in shown in this U.S. Specification and the composition of the HTD glass falls within this region.

In preparation of the HTD glass, to remove ion, spectrosil silica in predigested in concentrated hydrochloride acid, contained in an evaporating dish. The mixture is then heated in the evaporating dish on a boiling water bath and washed ten times with water. The procedure is repeated if the yellow colouration remains. The other constituents are obtained by using analytical reagent standard lithium carbonate, lanthanum nitrate, cesium carbonate and calcium carbonate.

The glasses are preignited in a platinum crucible by heating carefully with a meker burner, and then heated in an electric furnace till molten. The glass is held approximately at 50° C. in excess of the melting temperature for 5 hours. The glass may be poured from the crucible to form sticks. The sticks are then broken down in a percussion mortar and finely ground in an agate mortar with screening to 325 BSS.

Quite a number of resins have proved satisfactory for low temperature work but for electrodes used in excess of 100° C. Araldite resin AY103 and Hardener HT972 is preferred, using the procedure recommended in CIBA instructions sheet No. A22a and A15d.

Another possibility is to use silicone rubber, SR300, as the inert material in the mix.

Electrodes for use mainly at high temperatures are prepared by curing the resin firstly at 180° C, for 3 hours and then post curing for a further period of 3 hours at a temperature 10° – 20° C. in excess of the required maximum temperature of use. When cured the resin ranges from yellow to brown in colour. The electrodes are conditioned in 0.1 m. HCl for at least 24 hours to promote the formation of a hydrated layer; the resin ranges then in colour from green to brown.

In order to approach the ideal response of the hydrogen electrode it is necessary to ensure that each electrode using glass particles in the matrix contains at least 50% by weight of glass. It is in any case difficult to achieve a much higher percentage since the matrix material will in most cases not solidify with greater percentage. Mica being a less dense material, the maximum percentage by weight possible is approximately 40%. However as has been mentioned electrodes with lower percentages of ion sensitive material are extremely useful in some applications. A number of electrodes of the "ideal" type will now be described, although it will be appreciated that they can also be of the "diminished" type if the concentration of ion sensitive material is reduced. Later a number of primarily "diminished" electrodes will be described.

Figure 1A:
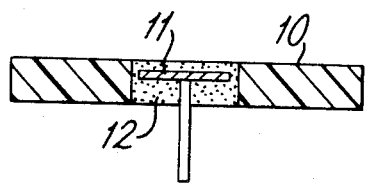

In FIG. 1(a) a disc shaped electrode consists of a PTFE or pure resin mould 10, "T" shaped platinum spade 11 and a matrix of resin 12 containing ion sensitive material. The ion sensitive material may be any of the materials mentioned above ground down to small particles.

In making the electrode, the platinum spade 11 is positioned in the centre of the mould 10, resin in introduced around it and the ion sensitive material-resin mix is also applied to the spade. The materials are then cured and after curing the electrode is usually free from cracks and voids.

Sometimes the ion sensitive material disperses throughout the surrounding resin and reduces the concentration of ion sensitive material in the area between the space 11 and the upper surface of the electrode as shown in FIG. 1(a). To reduce the effect of dispersion, the resin part of the electrode may be present and cured before the introduction of the ion sensitive material-resin mix. This latter method may also be varied by dropping more ion sensitive material on to the mix within the first 15 minutes of curing to increase the concentration of material in the active part of the electrode. Resin may also be applied to the spade and ion sensitive material dropped on to this resin, mixing being achieved by the action of gravity. However using this method air bubbles tend to become trapped in the mixture, some of which may be removed by evacuation.

Instead of the platinum spade 12 a copper spade of the same shape may be used. Such an electrode is not so expensive and has the advantage that a warning signal is given if the electrode fails by leakage, that is if the spade comes in direct contact with the electrolyte. In such circumstances the potential of the electrode changes dramatically because copper is readily attacked by either acids or alkalis.

Figure 1B:
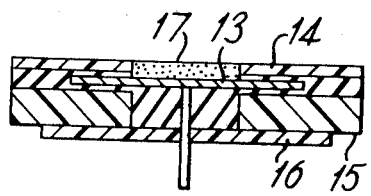

Another electrode is shown in FIG. 1(b) and consists of a "T" shaped metallic spade 13 which may for example be of platinum or copper positioned between two resin discs 14 and 15. The upper disc 14 is very thin being less than 0.001 inch thick, and the lower disc has an aperture for the stem of the spade 13 with a PTFE sheet 16 fixed across the aperture. The space between the discs is filled with silicone rubber and the area 17 above the central portion of the cross-piece of the spade 13 is filled with an ion sensitive material-silicone rubber mix. The silicone rubber is cured in air at room temperature and this process is complete in 24 hours.

Figure 2:
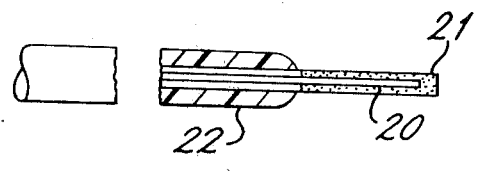
FIG. 2 shows a micro electrode according to the first aspect of the invention.

A micro electrode suitable for medical work is shown in FIG. 2; it consists of a platinum wire 20 with a coating of ion sensitive material-resin mix 21. A PTFE sleeve 22 is heat shrunk on to the resin coated wire and the connection is made within the sleeve to a long electrical conductor (not shown). The size of the electrode of FIG. 2 is limited solely by the size of the wire forming a substrate. The forms of the electrodes described in FIGS. 1(a), 1(b) and 2, and indeed all forms described require a roughening of the surface by emery, file etc. prior to the other essential preconditioning acid treatment. The roughning of the surfaces exposes the active pH particles by removing resin coating from the particles.

Figure 3:
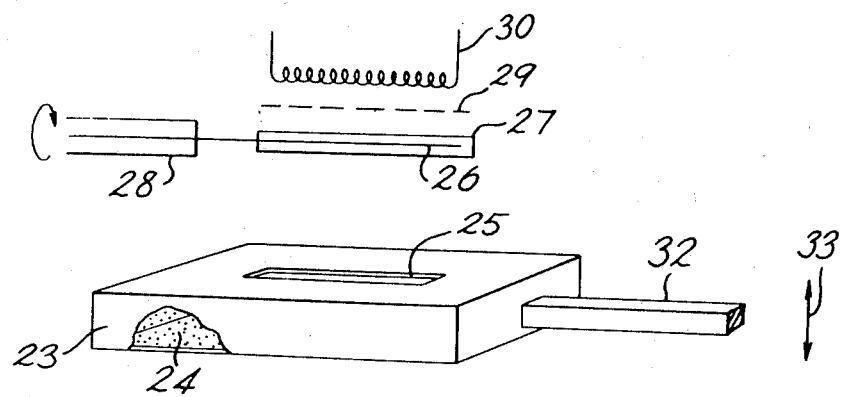
FIG. 3 shows apparatus for aligning ion sensitive particles in the construction of electrodes.

As has been mentioned electrical resistance is an important factor in the utility of ion sensitive electrodes. Equipment for use in constructing a rod electrode of the type described in connection with FIG. 2 is shown in FIG. 3. However this apparatus may be adapted to be used for other types of electrodes such as those of FIGS. 1(a) and 1(b). A box 23 has a metal plate 24 on its lower surface and a slit 25 in its upper surface. A wire 26 surrounded with resin 27 is mounted on a metal rod 28 which is rotated about its longitudinal axis by a slow speed motor (not shown). A metal screen or grid 29 is positioned between the resin coated wire 26 and a heater 30. An EHT supply (not shown) is connected between the metal plate 24 and the rod 28. The EHT supply may be an induction coil or any high-frequency low current device. The box 23 is vibrated by a solenoid (not shown) attached to an arm 32 which the solenoid moves in the directions of the double headed arrow 23.

The object of the apparatus of FIG. 3 is to deposit particles in an ordered orientation on the surface of the resin coating the wire 26. This ordered orientation reduces the resistance of the electrode which is an important factor in the utility of ion sensitive electrodes. Particles of ion sensitive material are placed on the metal plate inside the box. Here they become charged and move under the influence of the electric field between the plate and the wire 26 coupled to the rod 28. In moving through the slit following the lines of the electric field, the particles are deposited on the resin in the required ordered orientation.

The heater 30 is provided to cure the resin as the rod rotates and the metal screen 29 electrically connected to the rod 28 helps to prevent particles reaching and being deposited on the heater. Vibration of the box 23 helps to provide the initial movement for the particles and to ensure that there is an adequate supply of particles below the slit 25.

Figure 4A:
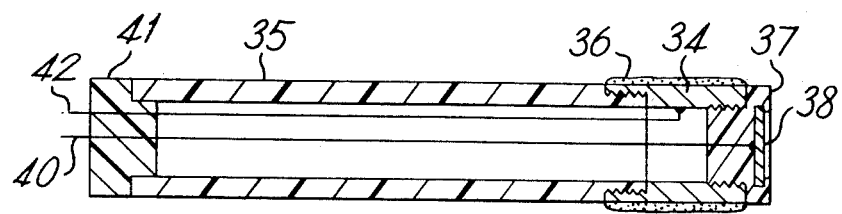
FIGS. 4(a) and 4(b) show probes each including an electrode according to the first aspect of the invention and a reference electrode.

A pH sensor for use in chloride containing solutions in shown in FIG. 4(a). A copper cylinder 34 is screwed to a PTFE cylinder 35 and the exterior of the copper cylinder is coated with a matrix 36 of pH material and resin. A PTFE annulus 37 contains a fused silver-silver chloride electrode 38 which has an electrical connection 40 passing through a push-fit PTFE plug 41 to the exterior of the electrode. A further connection 42 connected to the interior of the copper cylinder 34 also passes through the plug 41.

In operation where the pH value of the chloride containing solution is to be measured, the electrode of FIG. 4(a) is partially immersed, copper-cylinder end down, in the solution and the potential between the electrodes 40 and 42 is measured in the usual way. The potential between the wires 40 and 42 provides after subtraction of the potential due the silver-silver chloride electrode, or, more usually, by making use of a previous calibration of the electrode and measuring instrument with known pH buffers, an indication of the pH value of the solution.

Where changes in pH are alone required and not the absolute value, no calibration is necessary. The change in pH is followed by the emf between the wires 40, 42 and is equal to 59mV/pH change at 25° C., or some predetermined emf change/pH i.e. if the electrode has not ideal but a diminished response. The correct functioning of the electrode of course assumes that the chloride concentration remains constant, when used in the above manner.

Figure 4B:
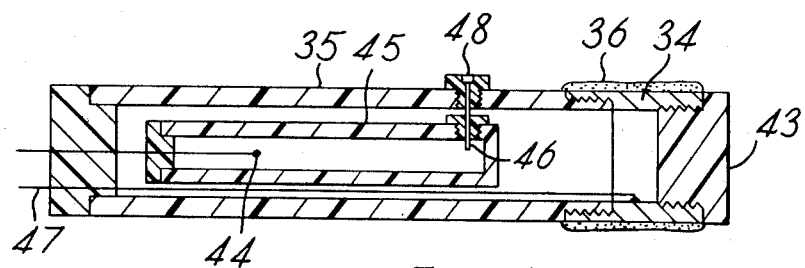

A somewhat similar type of pH sensitive electrode is shown in FIG. 4(b). Again the main body of the electrode is formed by a PTFE cylinder 35, which has, at one end, a copper cylinder 34 coated with a matrix 36 of resin containing pH sensitive material. A solid PTFE plug 43 replaces the silver-silver chloride electrode which is now situated at 44 in a PTFE cylinder 45 in the interior of the cylinder 35. The cylinder 45 contains may chloride containing solution, for example saturated KCL. It is connected by way of a rigid PTFE microbore tube 46 to a sintered PTFE plug 48. An interface is formed between the chloride solution in the tube 46 and any solution whose pH value is to be measured surrounding the cylinder 35 through the porosity of the sintered plug 48. Measurement of pH value of a solution is derived from the emf generated between the electrode 44 and a wire 47. The solution under study need not contain chloride. The liquid junction potential set up at the interface between the plug 48 and the solution is maintained practically constant because of the fine pores of the sinter. For normal use the electrode unit is calibrated with the measuring instrument using known pH buffers in the usual manner. The unit is immersed vertically until the solution under study covers the plug 48, i.e. about half the total length of the body of the unit.

Figure 5:
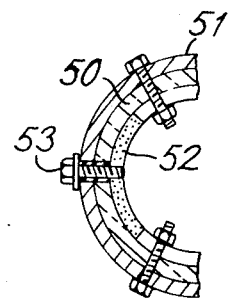
FIG. 5 shows an electrode according to the first aspect of the invention constructed to monitor the pH of liquid flowing in a pipe.

A useful robust day-to-day corrosion protection or monitoring pH electrode is shown in FIG. 5. The electrode is formed with a metallised piece of curved cast ceramic 50 bolted to the interior of a metal pipe 51. A coating 52 of pH material is a resin matrix is painted on to the metallised surface of the ceramic 50. An electrically insulated contact 53 is made to the electrode by way of the metallised surface beneath the resin matrix. In use the potential developed between an insulated contact for the matrix and a counter electrode which may be the pipe itself is monitored and any changes in this potential are an indication of change in pH value of liquid flowing through the pipe. In another application the pipe may be used as a working electrode, in corrosion monitoring and the ion sensitive electrode as a reference. A similar arrangement may find application attached to the legs of structures supported on the sea bed, such as oil rigs.

The electrodes described above may be used with any other suitable reference electrodes and the design of cells or apparatus for ion concentration measurement can take many forms as evidenced by the numerous publications on this subject. Many of these earlier forms may be adapted to the present electrodes and those familiar with the art will have little difficulty in finding many ways in which known cells and known methods can be adapted to use the new electrodes. However two cells will now be described by way of example with reference to FIGS. 6(a) and 6(b) and a measurement procedure will be briefly outlined. Another suitable cell and procedure is described in the paper by J. V. Dobson, R. E. Firman and H. R. Thirsk in the Journal of Physics E. Scientific Instruments 1973 Volume 6, pages 24 to 26.

In FIG. 6(a) a disc electrode 55 having a surface 56 formed by a matrix of material containing ion sensitive particles faces the interior of a chamber 57 containing an electrolyte whose ion concentration is to be measured. A suitable reference electrode, in this case a silver-silver chloride electrode 58 is immersed in the electrolyte. The electrolyte is pumped continously through the cell by way of an entry port 59 and an exit port 60. Potentials between a wire 61 and a wire 62 in connection to the matrix are measured using conventional equipment for high impedance ion selective electrodes, such as that mentioned in the paper by Dobson, Firman and Thirsk referred to above.

The form of measuring cell shown in FIG. 6(b) is for use at high pressure. It is similar to that shown in FIG. 6(a) except that the Viton O-ring 63 is surrounded by silicone rubber 64, the exit and entry ports are sealed with PTFE plugs 65 and 66 and a PTFE pressure sensitive bag 67 is coupled by way of a port 68 to the interior of the chamber 57. In addition a seal 69 is provided for the wire 61. When the effect of pressure is to be determined, the whole cell is placed in a pressure container and the pressure in the container is raised and transmitted to the interior of the chamber 57 by way of the PTFE bag 67.

The measurement procedure which is adopted with the cells of FIG. 6(a) and 6(b) is to introduce different concentrations of electrolyte into the cell and meausre the change in cell potential appearing between the wires 61 and 62. Steady state potentials are then measured, that it the linear portions of the curve shown in FIG. 7(a), and these linear portions are extrapolated back to the instant when the solutions were changed in order to find the intercept 71 giving the change in cell potential corresponding to the change in solution concentration.

FIG. 7(a) is for the cell Ag, AgCl/mHCl/disc pH electrode C3P-R1 (this code is explained below) of FIG. 1(a). The change in concentration occurring at about 90 minutes in FIG. 7(a) was from a 0.02 m HCl solution to a 0.01 m HCl solution. The change in cell potential is, of course, due both to the ion sensitive electrode and also to the reference electrode.

Where the transfer cell of the paper by Dobson, Firman and Thirsk is used instantaneous values of potential may be measured since the transients obtained are considerably shorter and may under the right conditions be of the order of seconds instead of minutes. For example FIG. 7(b) shows the variation of emf, corrected for incomplete washings in the way described in the above mentioned paper, with transfer length, that is the time for which each electrolyte was present in the transfer cell. For each point X in FIG. 8 the transfer was the same: from one solution of known concentration to another solution of different but known concentration. It will be seen that the transfer length had little effect on corrected emf change.

Instantaneous or steady state values may also be used with the dip type of elecytrodes shown in FIGS. 4(a) and 4(b) depending on measurement conditions, type of matrix used, diminished or ideal response and the precison required.

Some other examples of change in cell emf for different changes in HCl concentration at 25° C. are shown in Table 1 for cells containing the disc electrodes of FIGS. 1(a) or 1(b), and a silver-silver chloride reference electrode.

TABLE 1

| pH Electrode | % Weight of pH material | Solution change mHCl | time minutes | change in emf of pH electrode mV Actual | change in emf of pH electrode mV Theoretical |
|---|---|---|---|---|---|
| (RM-R1) FIG. 1(a) | 38 – 40 | 0.01 – 0.015 | 30 | – 2.8 | – 10.5 |
|  |  | 0.01 – 0.05 | 30 | – 7.1 | – 39.0 |
|  |  | 0.01 – 0.10 | 30 | – 12.2 | – 55 |
|  |  | 0.015 – 0.05 | 30 | – 7.2 | – 29 |
|  |  | 0.015 – 0.10 | 30 | – 10.5 | – 46 |
|  |  | 0.01 – 0.10 | 120 – 180 | – 28.5 | – 55 |
| (PG-R1) FIG. 1(a) | 67 | 0.01 – 0.02 | 30 | – 6.2 | – 20.8 |
|  |  | 0.01 – 0.10 | 40 – 60 | – 29.4 | – 55 |
| (PG-R2) FIG. 1(a) | 70 | 0.01 – 0.02 | 30 – 40 | – 5.6 |  |
| (C3P-R1) FIG. 1(a) | 66 | 0.01 – 0.10 | 120 | – 51.0 | – 55 |
| (C3P-SR1) FIG. 1(b) | 55 – 60 | 0.01 – 0.10 | 60 – 70 | – 50.9 | – 55 |
| (CO15-R1) FIG. 1(a) | 55 – 60 | 0.01 – 0.10 | 40 – 60 | – 10.0 | – 55 |
| (CO15-R2) FIG. 1(a) | 61 | 0.01 – 0.10 | 40 – 70 | – 7.5 | – 55 |

In Table 1 above the following code is used to identify the types of materials used in the disc electrodes:

RM — ruby mica,
PG — Perley glass,
C3P — Corning triple purpose glass
C015 — Corning 015 glass
R1 — resin matrix (Araldite AY103 with hardener HT972)
R2 — resin matrix (Araldite AY103 with hardener HY951)
SR1 — silicone rubber matrix.

It should be noted that the penultimate column of Table 1 gives the potential response obtained from a pH electrode after allowance had been made for the potential of the silver-silver chloride electrode.

The measurements shown in Table 1 show that the time to reach a steady date condition varied from 3 hours to 30 minutes. A steady state extrapolation procedure was used to determine the change in cell potential.

The theoretical value of cell potential for concentration changes $C_1$ to $C_2$ mHCl is given by:

$$\Delta E = - \frac{RT}{F} \log_e \frac{a_{HCl(2)}}{a_{HCl(1)}}$$

see "Ion Selective Electrodes", R. A. Durst (Editor) N.B.S. Special Publication No. 314, Washington Government Printing Office, 1969; where R = the gas constant, T = The absolute temperature, F = Faraday Constant 96500 Coulombs and $a$ is the activity of HCl, $m$ is the molality expressed as mol. kg$^{-1}$, The subscripts (2) and (1) refer to solutions 2 and 1 of different concentration, e.g. for $m_1$ to $m_2$ of 0.01 to 0.1 m HCl, $\Delta E \approx -112$ mV. The value obtained in this way is slightly different and more accurate from that obtained by using the expression

$$\Delta E = \frac{-RT}{F} \log_e \frac{m_{HCl(2)}}{m_{HCl(1)}},$$

which for the same concentration change would be 118mV.

In general having found the potential change occurring in a measuring cell containing an ion sensitive electrode for the change occurring in the potential of such an electrode, when a known electrolyte is replaced by an unknown, one of three methods can be used to find the required concentration: firstly comparison with graphs such as that of FIG. 8, secondly comparison of the potential change with changes previously obtained with known electrolytes, and thirdly direct calculation from one of the above expressions, preferably the first. In some circumstances, for example monitoring industrial waste, the normal potential is the known and any departure is an indication that a change whose approximate extent can be estimated has occurred.

The performance of a number of electrodes according to the invention with change in $$\log_e \left( \frac{a_{H^+}(m)}{a_{H^+}(0.01)} \right),$$

after allowing for the contribution due to change in chloride ions, is shown in FIG. 8. The response of an ideal hydrogen electrode is shown at 72 and that of a disc electrode including Corning triple purpose glass in resin or silicone rubber is shown at 73. The response of a disc electrode using Perley glass in a resin matrix is shown at 74 and that of a ruby mica electrode with resin is shown at 75. All the electrodes mentioned in connection with FIG. 8 are constructed according to FIG. 1(a) except that containing Corning triple purpose glass in silicone rubber which is of the type shown in FIG. 1(b).

Corning triple purpose glass, which is shwon to have an ideal pH response when used as a conventional glass electrode, is also seen from Table 1 and FIG. 8 to have an almost ideal pH response when used as a disc electrode. On the other hand the ruby mica electrode has a low pH response of approximately minus 13mV/pH unit. This low response is an important factor in constructing diminished response electrode as will be mentioned later.

Having demonstrated in Table 1 and FIG. 8 that electrodes according to the invention function satisfactorily, some examples of operation at high temperatures and pressures will now be given in connection with FIG. 9. As, perhaps would be expected, it has been found that electrodes having enhanced chemical durability at elevated temperatures and pressures have a more stable potential under such conditions. For example, a cell having a silver-silver chloride electrode and a disc electrode containing Corning 015 glass in a resin matrix has a very stable potential at 25° which changes at a rate of only about 4Mv/hour, but at 150° C and a pressure of 50 bars the potential of this cell changes by several hundred millivolts over several hours. On the other hand a cell having the same reference electrode and disc electrode with ruby mica in a resin matrix was found to vary by about 10mV per hour at 25° and one bar, but by a smaller amount at 150° C. and 50 bars. For these tests the apparatus of FIG. 6(b) was used, the electrolyte being 0.01 m HCl. The graphs 76, 77 and 78 of FIG. 9 give the stability at 50 bars and temperatures of 60° C., 100° C. and 206° C, respectively, of a disc electrode of the type shown in FIG. 1(a) using HTD glass in a resin matrix. The stability at 150° C. of a cell containing a ruby mica in resin disc electrode is shown at 79. Thus cells containing disc electrodes employing chemicaly durable pH sensitive materials have stable potentials up to 206° C. and the rates of change of cell potential with time are always less than 30 millivolts per hour, sufficiently low and stable that precise measurements could be made at elevated temperatures if the transfer cell previously referred to were used.

From Table 1 and FIG. 8 it can be seen that some electrodes have a response which is considerably diminished from the ideal. However, providing the response of the electrode to changes in concentration in linear it can still be used to indicate ion concentration. In fact these electrodes are useful in two ways, firstly to indicate ion concentration in the usual way, and secondly as reference electrodes. In general as electrolytes increase in temperature their proton concentration changes and it is helpful to have a reference electrode whose potential changes in approximately the same way. In this way automatic compensation for change in proton concentration is achieved and this is the role for diminished response ion selective electrodes as reference electrodes.

FIG. 10 shows a number of diminished response electrodes which are either two sided as in FIGS. 10(a), 10(b) and 10(e) or one sided as in FIGS. 10(c), 10(d) and 10(f).

A thin mica sheet 81 held rigidly between two members 82 and 83 of a PTFE support is shown in FIG. 10(a). A liquid tight joint is made between the mica sheet and support by using a neoprene gasket 84 and the two parts of the support are pressed rigidly together, when in use, by pressure applied from tightening bolts in a cell which is described later in connection with FIG. 11.

Mica sheets may also be mounted on Vitreosil silica discs as shown in FIG. 10(b) where the mica sheet 81 is fixed to a silica disc 85 with epoxy resin 86. Using an ultrasonic drill and a brass cutting tool, holes 7/16th of an inch in diameter are cut in the centres of silica discs, the discs being 30 millimeters in diameter and 4 millimeters thick. The discs are then abraded on one side with carborundum and cleaned by boiling firstly in one N hydrochloric acid and then in distilled water. They are next dried in an oven and the mica sheets mounted on the abraded sides over the central hole. For electrodes to be used 25° C. the epoxy resin is cured at 80° C. for 3 hours. The electrodes of FIG. 10(b) may also be used with the type of cell shown in FIG. 11(a), but only the mica face is exposed to the solution under investigation and the silica disc can be conveniently covered with a thin film of silicone rubber. In FIG. 10(e) the mica disc 81 is mounted between two silica discs 87 and 88 having central apertures. Again epoxy resin 89 is used to hold the mica disc to the silica discs.

The single sided electrode of FIG. 10(c) is somewhat similar to that of FIG. 10(a) in that is comprises a mica disc 81 and two members 82 and 83 of PTFE support. However, a platinum or copper spade 91 is also sandwiched between the two support members 82 and 83 and it may be found advantageous to silver, by evaporation prior to mounting, one side of the mica disc 81 to improve the contact between the disc and the spade 91.

In FIG. 10(d) an electrical connection 92 is made to a mica sheet 81 using a fused silver halide contact. Simultaneously with fusing the silver chloride to the mica the end of a 28 gauge silver wiere 93 is introduced into the molten silver chloride. On cooling, the silver chloride becomes solid holding the silver wire firmly in position. To strengthen the silver halide connection, epoxy resin 94 is applied to the back of the mica sheet.

In preparation of the electrode of FIG. 10(f) ion sensitive material is used in powder form, for example mica is ground to a fine powder using an Agate mortar and pestle and mixed with the epoxy resin. The mixture is applied to a platinum spade 95, positioned in a hole in the centre and slightly below one surface of a silica disc 96, as shown. The mica particle size is approximately 2 to 20 micrometers and the mixture is cured for a minimum of 3 hours at 80° C. For diminished response the concentration of ion sensitive material in the matrix should be less than approximately 50% by weight.

As with the earlier described electrodes, many of the known methods and techniques for using ion sensitive electrodes may be modified in using the electrodes of FIG. 10. It will also be apparent that the type of reference electrode to be used will depend on the solution whose ion concentration is to be found. However, the two cells of FIGS. 11(a) and 11(b) will now be briefly described in order to show one way in which the electrodes of FIG. 10 can be used when an electrolyte contains chloride ions and therefore a silver-silver chloride reference electrode may be used.

For double sided electrodes, the two parts 82 and 83 of the mica sheet support are pressed together by bolts 98 joining two PTFE chambers 99 and 100 to allow the mica disc to be exposed to both solutions and thus to act as a pH electrode in both solutions. Viton O rings 102 and 103 ensure a liquid tight seal to the chambers 99 and 100. Each chamber contains a silver-silver chloride electrode 104, and entry and exit ports 106 and 107, respectively.

In operation a solution of known hydrogen ion and chloride ion concentration is introduced into one of the chambers 99 and 100 and an unknown solution is introduced into the other chamber, the potential between the two silver chloride electrodes giving an indication of the concentration of hydrogen ions in the unknown electrolyte.

Where single sided electrodes are used the cell of FIG. 11(b) is suitable. The left hand half of this cell is the same as that shown in FIG. 11(a) but the right hand half is replaced by a PTFE member 110 which replaced the chamber 99 and helps to hold the two parts of the electrode support together. A PTFE plug 111 is screwed into the member 110 and has central bore for the wire 93 from the single sided electrode. To measure the concentration of hydrogens ions in an electrolyte, a known electrolyte is first introduced into the chamber 100 and the potential between the electrode 104 and the wire 93 is measured. The unknown electrolyte is then used several times to wash out the chamber 100 which is then filled with the unknown electrolyte and the cell potential again measured. Change in potential, of course, giving the required indication of hydrogen ion concentration in the unknown solution in the manner described previously.

Cells of the type shown in FIGS. 11(a) and 11(b) using the electrodes of FIG. 10 have been found to have a change of minus 60 mV on everage in response to the 0.01 to 0.01 m HCl solution change. When the contribution of the silver-silver chloride electrode is subtracted this leaves minus 12 mV for the ruby mica electrode response. Cells containing white mica electrodes have a mean change of minus 65 MV for a similar solution change and after subtraction of the contribution of the silver-silver chloride electrode, minus 9 mV is found to be the white mica electrode response.

While the number of different electrodes and methods of use have been described it will be apparent that the invention can be put into practice in many other ways, for example by using material sensitive to different ions, by using other materials than those specified as the matrix material and by using different configurations of electrodes. Other known types of reference electrode may be used with suitable electrolytes.

I claim:

1. Ion sensitive electrode means, including a matrix of low conductivity material containing particles of an ion sensitive material selected from the group consisting of a finely divided ion sensitive glass and a finely divided mica, the ion sensitive material having an outer hydrated layer thereon, and contact means for allowing direct electrical coupling with the interface formed when the matrix is in contact with a liquid.

2. Electrode means according to claim 1 wherein the ion sensitive material is a finely divided ion sensitive glass.

3. Electrode means according to claim 2 wherein the ion sensitive glass is selected from the group consisting of boro-silicate glass, mixed alkali lead glass, alkali silicate glass and alkali-alkaline earth glass.

4. Electrode means according to claim 3 wherein the ion sensitive glass is an alkali silicate glass selected from the group consisting of soda glass and lithia glass.

5. Electrode means according to claim 2 which is sensitive to the H+ ion wherein the ion sensitive material is a finely divided glass selected from the group consisting of:
 a glass having the composition 27 to 29 mole % $Li_2O$, 2 to 4 mole % $Cs_2O$ and/or $Rb_2O$, 4 to 7 mole % $La_2O_3$, 1 mole % $UO_2$ and balance $SiO_2$;
 a glass having the composition 22 mole % $Na_2O$, 6 mole % $CaO$ and 72 mole % $siO_2$; and
 a glass having the composition 65% $SiO_2$, 28% $Li_2O$, 4% $La_2O_3$ and 3% $CsO_3$ by weight.

6. Electrode means according to claim 2 which is sensitive to the H+ ion wherein the ion sensitive material is a high temperature glass including $Li_2O$, $CaO$ and $SiO_2$.

7. Electrode means according to claim 6 wherein the high temperature glass has the composition 55% $SiO_2$, 27% $CaO$ and 18% $Li_2O$ by weight.

8. Electrode means according to claim 6 wherein the high temperature glass has the composition 55±5% $SiO_2$, 27±5% $CaO$ and 18±5% $Li_2O$ by weight.

9. Electrode means according to claim 2 wherein the glass is soda glass having the composition 24.4% $Na_2O$, 6.4% $CaO$ and 72.2% $SiO_2$.

10. Electrode means according to claim 2 wherein the ion sensitive glass is a ternary glass containing $SiO_2$ and $Na_2O$ or $Li_2O$, together with a compound selected from the group consisting of $K_2O$, $SnO_2$, $B_2O_3$, $ZnO_2$, $Al_2O_3$ and $Ga_2O_3$.

11. Electrode means according to claim 2 wherein the ion sensitive glass is ternary glass including three compounds, each chosen from a different one of first, second, third and fourth groups, the first group consisting of $Sb_2O_3$, $TiO_2$, $ZrO_2$, $GeO_2$, $SnO_2$ and $PtO_3$, the second group consisting of $CaO$, $MgO$ and $BeO$, the third group consisting of $La_2O_3$, $Nb_2O_3$ and $Y_2O_3$ and the fourth group consisting of $Al_2O_3$, $B_2O_3$, $Ga_2O_3$ and $Fe_2O_3$.

12. Electrode means according to claim 1 wherein the ion sensitive material forms at least 50% by weight of the low conductivity material and ion sensitive material together.

13. Electrode means according to claim 1 wherein the ion sensitive material forms at least 40% by weight of the low conductivity material and the ion sensitive material together.

14. Electrode means according to claim 1 wherein the low conductivity material has a specific resistance in the range $10^9$ to $10^{12}$ ohm centimeters.

15. Electrode means according to claim 14 wherein the low conductivity material is
    an epoxy resin or
    a silicone rubber.

16. Electrode means according to claim 1 wherein the direct contact means includes a conductive member in contact with the matrix and having an electrical connection thereto.

17. Electrode means according to claim 16 wherein the material of the conductive member includes a metal selected from the group consisting of
    copper; and
    platinum.

18. Electrode means according to claim 16 including a body having inert surface material, the body defining an aperture, the conductive member and the matrix being positioned in the aperture with the matrix having access to the exterior of the body.

19. Electrode means according to claim 18 which is sensitive to the H+ ion, wherein the ion sensitive material is a finely divided glass selected from the consisting of
    a glass having the composition 27 to 29 mole % $Li_2O$, 2 to 4 mole % $Cs_2O$ and/or $Rb_2O$, 4 to 7 mole % $La_2O_3$, 1 mole % $UO_2$ and balance $SiO_2$;
    a glass having the composition 22 mole % $Na_2O$, 6 mole % CaO and 72 mole % $SiO_2$; and
    a glass having the composition 65% $SiO_2$, 28% $Li_2O$, 4% $La_2O_3$ and 3% $CsO_3$ by weight.

20. Electrode means according to claim 18 wherein the body includes an annular resin disc, the conducting member is disc shaped and positioned with the matrix in the aperture of the resin disc, and the electrical connection passes into the said aperture where it is connected to the conducting member.

21. Electrode means according to claim 18 wherein the body includes two annular resin discs, the conducting member is disc shaped and interposed in a silicone rubber layer between the resin discs, the aperture of one disc contains the matrix, and the electrical connection to the conducting member passes through the aperture in the other disc which is otherwise filled with silicone rubber.

22. Electrode means according to claim 18 wherein the body includes an annular silica disc covered with inert material, the conducting member includes a disc shaped portion within the aperture of the disc, the aperture also contains the matrix, and the ion sensitive material is a finely divided naturally occurring mica.

23. Electrode means according to claim 1 wherein the contact means includes a conductive substrate and the matrix is coated on the substrate.

24. Electrode means according to claim 23 wherein the substrate is a metal wire.

25. Electrode means according to claim 23 wherein the substrate is the metallized surface of a ceramic member adapted for fixing to the interior surface of a pipe.

26. Electrode means according to claim 1 mounted on the exterior of a probe member having a reference electrode also mounted thereto.

27. Electrode means according to claim 26 which is sensitive to the H+ ion, wherein the ion sensitive material is a finely divided glass selected from the group consisting of
    a glass having the composition 27 to 29 mole % $Li_2O$, 2 to 4 mole % $Cs_2O$ and/or $Rb_2O$, 4 to 7 mole % $La_2O_3$, 1 mole % $UO_2$ and balance $SiO_2$;
    a glass having the composition 22 mole % $Na_2O$, 6 mole % CaO and 72 mole % $SiO_2$; and
    a glass having the composition 65% $SiO_2$, 28% $Li_2O$, 4% $La_2O_3$ and 3% $CsO_3$ by weight.

28. Electrode means according to claim 26 wherein the probe member includes a first cylindrical member, the contact means includes a conducting second cylindrical member of substantially the same diameter as the first cylindrical member and fixed coaxially at one end thereof, the reference electrode being mounted at that end of the second cylindrical member which is remote from the first cylindrical member, and electrical connections for the conducting second member and the reference electrode pass through the first cylindrical member.

29. Electrode means according to claim 26 wherein the probe member defines an interior chamber for an electrolyte and contains a reference electrode, the probe member including a passage from the interior chamber to the exterior of the member, and a porous plug extending to fill a portion of the passage.

30. Electrode means according to claim 29 wherein the probe member includes a hollow first cylindrical member, the contact means includes a conducting second cylindrical member of substantially the same diameter as the first cylindrical member and fixed coaxially at one end thereof, and electrical connections for the conducting second member and the reference electrode pass through the first member.

31. Electrode means accordingly to claim 1 wherein the ion sensitive material is a finely divided naturally occurring mica.

32. Electrode means according to claim 31 wherein the mica is ruby mica.

* * * * *

Disclaimer 4,052,285.—*John Vincent Dobson*, Hartlepool, England. ION SELECTIVE ELECTRODES. Patent dated Oct. 4, 1977. Disclaimer filed Oct. 15, 1980, by the assignee, *National Research Development Corporation*.

Hereby enters this disclaimer to all claims of said patent.

[*Official Gazette January 6, 1981.*]